(12) United States Patent
Zhao et al.

(10) Patent No.: US 8,680,232 B2
(45) Date of Patent: Mar. 25, 2014

(54) PREPARATION METHOD OF PIMARIC ACID TYPE RESIN ACID

(75) Inventors: Zhendong Zhao, Nanjing (CN); Yuxiang Chen, Nanjing (CN); Liangwu Bi, Nanjing (CN); Yan Gu, Nanjing (CN); Dongmei Li, Nanjing (CN); Jing Wang, Nanjing (CN); Yanju Lu, Nanjing (CN)

(73) Assignee: Institute of Chemical Industry of Forest Products, CAF, Nanjing, Jiangsu (CN)

( * ) Notice: Subject to any disclaimer, the term of this patent is extended or adjusted under 35 U.S.C. 154(b) by 117 days.

(21) Appl. No.: 13/254,774

(22) PCT Filed: Mar. 18, 2010

(86) PCT No.: PCT/CN2010/071134
§ 371 (c)(1),
(2), (4) Date: Sep. 2, 2011

(87) PCT Pub. No.: WO2010/105574
PCT Pub. Date: Sep. 23, 2010

(65) Prior Publication Data
US 2012/0004390 A1 Jan. 5, 2012

(30) Foreign Application Priority Data
Mar. 20, 2009 (CN) .......................... 2009 1 0030374

(51) Int. Cl.
*C09F 1/02* (2006.01)
(52) U.S. Cl.
USPC ........................................................ 530/204
(58) Field of Classification Search
USPC ........................................................ 530/204
See application file for complete search history.

(56) References Cited

U.S. PATENT DOCUMENTS 3,562,243 A 2/1971 Aldrich
3,658,891 A 4/1972 Gonis et al.

FOREIGN PATENT DOCUMENTS

| CN | 101020630 A | 8/2007 |
| CN | 101302151 A | 11/2008 |
| CN | 101508871 A | 8/2009 |

OTHER PUBLICATIONS

Zubrick, The Organic Chem Lab Survival Guide, 1988, Extraction and Washing, p. 112-128.*

(Continued)

*Primary Examiner* — Liam Heincer
*Assistant Examiner* — Nicholas Hill
(74) *Attorney, Agent, or Firm* — Christie, Parker & Hale, LLP

(57) ABSTRACT

A method for preparing pimaric acid type resin acids includes the following steps: step (1) adding refined resin acid, turpentine, or rosin along with maleic anhydride at a mass ratio of 1:0.3-1.5 into a reaction bottle, dissolving the ingredients into a $C_1$-$C_{10}$ lower fatty acid solvent, the mass ratio of the $C_1$-$C_{10}$ low fatty acid to refined resin acid is 0.05-30:1, then carrying out additional reaction by heating directly or with assistance of a microwave, subsequently cooling, crystallizing, filtering, and washing; and step (2) combining the filtrates collected in step (1), stripping the solvent by vacuum distillation to obtain pimaric acid type resin acid coarse product, dissolving the resulting coarse product in NaOH aqueous solution to prepare aqueous solution of pimaric acid type resin acid salt, adjusting the pH level to 6-14 with a mineral acid or an organic acid while stirring, and either directly purifying or acidifying followed by purifying, the resulting precipitation to obtain the final product. The method has the characteristics of high yield, high product content, low cost, and low environmental pollution.

9 Claims, 1 Drawing Sheet

(56) References Cited

OTHER PUBLICATIONS

Wang et al., "Synthesis of maleopimaric acid under microwave radiation," Chemical Reagents, 2009, 31, 177-179; document added to the CAPLUS database on Mar. 30, 2009.*
Sasaki et al., "Excellent acceleration of the diels-alder reaction by microwave irradiation for the synthesis of new fluorine-substituted ligands of nmda receptor," Bioorg. Med. Chem. Lett., 1998, 8, 2983-2986.*
International Search Report, dated Jun. 17, 2010, corresponding to PCT/CN2010/071134, 7 pages.
Gonis, et al., "Preparation of Maleopimaric Acid," Ind. Eng. Chem. Prod. Res. Develop., vol. 12, No. 4, 1973, pp. 326-327.
Vesterburg, "Ueber Pimarsäuren" 1886, 19(2): 2167-2175, 1 page.
Vesterburg, "Ueber Pimarsäuren" 1887, 20(2): 3248-3253, 1 page.
Vesterburg, "Ueber Pimarsäuren" 1885, 18(2): 3331-3334, 1 page.
Sandermann, "Chemistry and Technology of Natural Resin, Turpentine, and Wood Pulp Oil Slick [M]," Beijing: China Forestry Publishing House, 1982:56, 5 pages, Partial English translation 1 page.
Palkin, et al., "The Resin Acids of American Turpentine Gum. The Preparation of the Pimaric Acids from *Pinus palustris*" American Chemical Society, Sep. 1933, 3677-3684, 8 pages.
Harris, et al., "Resin Acids. III. The Isolation of Dextropimaric Acid and a New Pimaric-type Acid, Isodextropimaric Acid" J. Am. Chem. Soc., 70, 2079, Jun. 1948, 2079-2081, 3 pages.
Baldwin, et al., "A New Method for Isolating Isodextropimaric Acid from Pine Oleoresin and Rosin," American Chemical Society, Jan. 1958, 25-26, 2 pages.

* cited by examiner

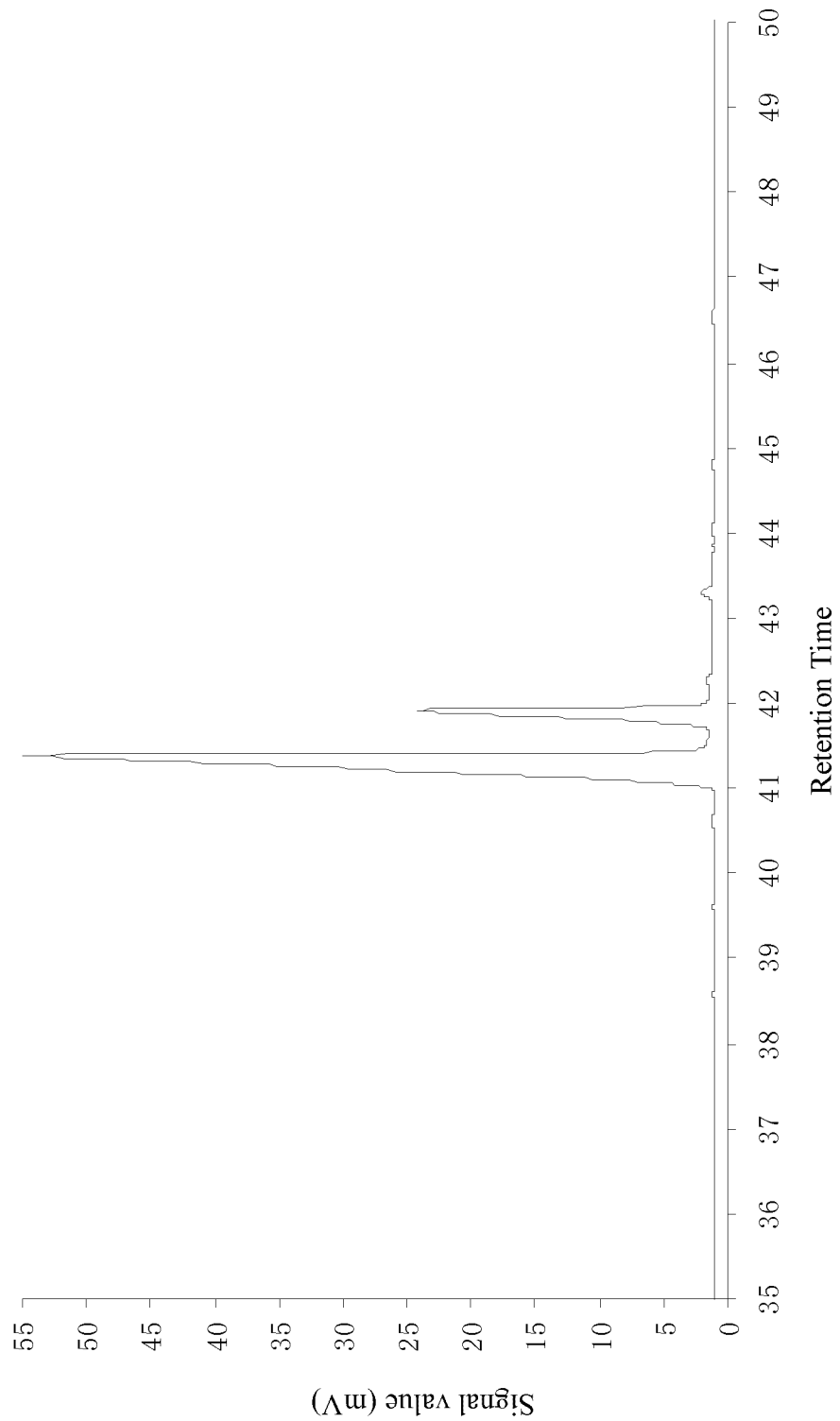

PREPARATION METHOD OF PIMARIC ACID TYPE RESIN ACID

CROSS-REFERENCE TO RELATED APPLICATION(S)

This application is a National Phase Patent Application and claims the priority to and benefit of International Application Number PCT/CN2010/071134, filed on Mar. 18, 2010, which claims priority of Chinese Patent Application Number 200910030374.7, filed on Mar. 20, 2009.

FIELD OF THE INVENTION

The present invention relates to a process for preparing resin acid, in particular pimaric type resin acid, from pine oleoresin or rosin.

BACKGROUND OF THE INVENTION

Pine oleoresin is mainly comprised of a series of unsaturated diterpene carboxylic acids, except turpentine, having a phenanthrene ring structure, a few neutral compounds, and a few fatty acids. These diterpene carboxylic acids have the same molecular formula $C_{20}H_{30}O_2$, and are generally known as resin acids. The resin acids mainly include abietic acid, palustric acid, levopimaric acid, neoabietic acid, dehydrogenated abietic acid, pimaric acid, isopimaric acid, and sandaracopimaric acid, etc. These resin acids can be divided into two categories: abietic type resin acids and pimaric type resin acids by chemical structure. The molecule of abietic type resin acid has two conjugated double bonds and one isopropyl. Abietic acid, palustric acid, levopimaric acid, and dehydrogenated abietic acid all belong to this category.

The molecule of pimaric type resin acid has a methyl and a vinyl at the position of $C_{13}$, and has two separate double bonds. This category mainly includes pimaric acid resin acids which are commonly seen in pine oleoresin and rosin, such as pimaric acid, isopimaric acid, sandaracopimaric acid, and other pimaric type resin acids which are rarely seen in the natural world, such as 8,15-isopimaric acid, Δ8(9)-pimaric acid, 7,15-pimaradiene-18-acid, etc.

Some components of pimaric type resin acids have biological activities against cancer, viruses, phlogosis, bacteria, and parasites, etc., and have potential therapeutic actions against diseases such as hypertension, tonic cystitis, allergic bronchitis, and chemical central nervous system disorders. They can also be transformed into derivatives by utilizing the active groups (e.g., carboxyl, exocyclic vinyl) in the molecular structure and can then be utilized again.

There are few reports on the research of the method for separation and preparation of some components in pimaric type resin acids:

(a) The following is a description of the alkali metal salt method [PALKIN S, HARRIS T H, The resin acids of American Turpentine Gum: The preparation of the pimaric acids from *Pinus Palustris* [J]. J Am Chem Soc, 1933, 55(9): 3677-3684; SANDERMANN W, Chemistry and Technology of Natural Resin, Turpentine, and Wood Pulp Oil Slick [M]. Beijing: China Forestry Publishing House, 1982:56]. In this method, pine oleoresin is treated by vacuum filtration first to obtain fresh resin acids, the resin acids are extracted with 80% ethanol, the residue of extraction is recrystallized with 95% ethanol to obtain the mixture of levopimaric acid and pimaric acid, and then the mixture is transformed into sodium salt which can be recrystallized to obtain pimaric acid. However, the yield of pimaric acid is only 3.3%. In this method, the temperature of extraction and crystallization must be controlled strictly, and pine oleoresin chosen as a raw material must ensure that the optical activity of sodium salt is higher than −160° C.

(b) The method reported by VESTERBERG A is: the crystallinic resin acid obtained from *galipia officinalis* resin or French rosin is first produced into pimaric ammonium salt, which is then transformed into pimaric sodium salt; finally, the pimaric sodium salt is recrystallized in 2% NaOH. However, the yield of this pimaric type resin acid is only 1.5% of galipia officinalis resin. In this method, pimaric acid experiences many transformation procedures; therefore, the loss is severe and the yield is low. This method is not suitable for large-scale preparation.

(c) The following is a description of the direct ammonium salt precipitation method [LOEBLICH V M, LAWRENCE R V, A new method for isolating isodextropimaric acid from pine oleoresin and rosin [J]. J Org Chem, 1958, 23(1): 25-26]. In this method, isopimaric ammonium salt is first precipitated directly from n-heptane solution of rosin with piperidine, then the ammonium salt is purified by fractional crystallization with 95% ethanol as the solvent, and finally, the ammonium salt is reduced to isopimaric acid. Although piperidine is selective to isopimaric acid, this method has a shortcoming in that the crystallization rate of the produced ammonium salt is very slow and the yield is low. Therefore, this method can only be used for research in small quantities.

(d) The flowing is a description of the method for preparing isopimaric acid. Recently, in Chinese Patent Application No. CN101302151A filed by ZHAO ZHENDONG, et al, a method for preparing isopimaric acid is disclosed. In this method, thermally isomerized rosin is dissolved in acetone, and treated with isobutanolamine to form a crude product of isopimaric ammonium salt. The isopimaric ammonium salt is purified by the multi-recrystallization method, then treated with acidification and ionization via hydrochloric acid, and finally refined and purified to obtain purified isopimaric acid. Although this method has advantages such as low cost and high yield, it is not suitable for preparing mixed pimaric type resin acids.

(e) The following is a description of the maleated derivatization method [HARRIS G C, SANDERSON T F. Rosin acids (III) The isolation of dextropimaric acid, a new pimaric-type acid, isodextropimaric acid [J]. J Am Chem Soc, 1948, 70(1): 2079-2085; ALDRICH P H, Process for separation of rosin adducts from mixtures with rosin: U.S. Pat. No. 3,562,243 [Patent], 1971]. In this method, ammonium salt is produced from the reaction between cyclohexylamine and resin acids; the ammonium salt is treated by crystallization, separation, and acidification to obtain a purified resin acid mixture; the resin acid mixture is catalyzed by saturated hydrogen chloride to react with maleic anhydride in benzene solvent under boiling conditions for 24 hours; after the benzene solvent is distilled, the residue is dissolved in concentrated alkaline solution; the pH of the solution is adjusted to 6.2 in order to make the unreacted resin acid crystallize; the unreacted resin acid reacts with butanolamine (2-amido-2-methyl-1-propanol) in acetone solution to obtain the crystalline of isopimaric ammonium salt; and finally the isopimaric ammonium salt is recrystallized with methyl acetate and treated by acidification, ionization, and purification to obtain isopimaric acid. ALDRICH et al studied several processes for separating maleated adducts, including crystallization with glacial acetic acid, dissolution and separation of carbon tetrachloride adduct, and dissolution by means of solvent polarity difference, etc. The target product of the above method is the isopimaric acid. One of the shortcomings of this method is long reaction time. Another shortcoming of this method is the difficulty in completely separating maleopimaric acid and unreacted resin acids, including pimaric type resin acids, dehydro abietic acid, and a small amount of abietic acid-type resin acid that is not thoroughly reacted, and the resulting product may contain maleopimaric acid. Moreover, wide use of benzene solvent and hydrogen chloride gas may cause serious environmental pollution and high requirements for the equipment.

(f) The following is a description of the benzoquinone derivatization method [SANDERMANN W, Chemistry and Technology of Natural Resin, Turpentine, and Wood Pulp Oil Slick [M]. Beijing: China Forestry Publishing House, 1982: 56]. In this method, the resin acids from pine resin are transformed into benzoquinone adducts which are then filtered, and the crystalline product obtained from the mother solution is crystallized in acetone and then recrystallized in both glacial acetic acid and methanol to obtain pimaric type resin acids. A drawback of this method is that the application approaches of the benzoquinone adducts are very limited, and therefore may cause loss of raw material and increased cost. This method needs further improvements in terms of economic efficiency.

(g) The following is a description of the rectification method [HARRIS G C, SANDERSON T F, Rosin acids (III) The isolation of dextropimaric acid, a new pimaric-type acid, isodextropimaric acid [J]. J Am Chem Soc, 1948, 70(1): 2079-2085]. In this method, fatwood rosin or gum rosin is rectified in a tower having 10 tower plates at 13.3 Pa pressure; the fraction with the boiling point between 136° C.-200° C. is taken to produce ether solution of sodium salt; the sodium salt is treated by acidification and the resin acids are dissolved in ether; and then, ether is removed to obtain concentrated pimaric acids and isopimaric acids. The drawbacks of this method include the high requirements for fractionation condition, which are adverse to operation, and the low yield of isopimaric acids and pimaric acids.

At present time, there is limited research and development on separation and purification of pimaric type resin acids in the world, and no published report on developing and utilizing pimaric type resin acids as a product. Nor is there any production of commercial pimaric type resin acid product or rosin product rich in pimaric type resin acid. Exploring high-efficiency, high-yield, and high economic feasibility methods for preparation of pimaric type resin acids will be beneficial to facilitate and speed up both the research and development of pimaric type resin acid products, especially in the application of medicine, biology, material, and other fields.

SUMMARY OF THE INVENTION

In view of the drawbacks in the prior art, such as low yields, severe environmental pollution, and high costs, etc., the present invention provides a method for preparing pimaric type resin acids, which has advantages such as high yield, high content, low costs, and less environmental pollution, etc., the method comprising the following steps:

Step 1: loading refined resin acids, pine resin, or rosin, along with maleic anhydride at a 1:0.3-1.5 mass ratio into a reaction flask; dissolving the ingredients into a $C_1$-$C_{10}$ lower fatty acid solvent such as glacial acetic acid, propionic acid, or butyric acid, wherein the mass ratio between $C_1$-$C_{10}$ lower fatty acid solvent and refined resin acids being 0.05-30:1; and then placing the mixture under either microwave-assisted heating or direct heating to further assist the reaction. After the reaction is complete, the mixture is cooled, crystallized, filtered, and washed. If the reaction is assisted using microwave-assisted heating, the microwave power is to be 100 W-50 kW, the reaction time is to be within 5 min-300 min, and the reactor is a special refractory reactor that doesn't absorb microwave and is equipped with a reflux condenser.

Step 2: Combining the filtrate collected in step 1, and then performing reduced pressure distillation to remove the solvent to obtain the crude product of pimaric type resin acids; then, dissolving the crude product of pimaric type resin acids in sodium hydroxide solution to produce a saline solution of pimaric type resin acids; then, adjusting the pH of the mixture to around 6-14 using mineral acid such as hydrochloric acid or sulfuric acid, or using organic acid such as formic acid or acetic acid during agitation; and then treating the obtained precipitate with direct purification or purification after acidification to obtain the final product of pimaric type resin acids, wherein the concentration of the sodium hydroxide solution is 0.5 wt %-40 wt % and the concentration of the acid is 0.5 wt %-100 wt %. The purification process includes dissolving the precipitate in ether with a mass of 0.5-20 times the mass of the precipitate; washing the dissolved mixture with water until the ether layer becomes neutral; drying the dissolved mixture with anhydrous magnesium sulfate; evaporating the ether at 1 atm; and finally drying the remains in a vacuum to obtain the product of pimaric type resin acids.

Refined resin acids are a form of purified resin acids and are obtained by removing the neutral substances in pine oleoresin or rosin through recrystallization in organic solvent, and either treating the obtained with sodium salt or ammonium salt, or washing the obtained with organic solvent. Specifically, dissolving 1 part by weight (pbw) of pine oleoresin or rosin into 2.5 pbw of petroleum ether while boiling at 60° C.-90° C.; removing insoluble solid impurities by filtering; removing water from the filtrate with a separatory funnel; and slowly adding cyclohexylamine solution in drops while agitating in order to produce a large quantity of white precipitate of ammonium salt of resin acid; agitating the mixture for 1 hour at 40° C.; cooling to room temperature—followed by further cooling down in an ice water bath; performing vacuum filtration; washing the precipitate with 0.2 pbw of petroleum ether three times; drying in a vacuum at 40° C.; grinding the white resin acid ammonium salt into powder; adding 0.7 pbw ether; adding 2 mol/L hydrochloric acid solution during agitation at room temperature until the white resin acid ammonium salt powder disappears completely, followed by 30 minutes of further agitation; transferring the mixture into a separate funnel to remove the water layer; washing with distilled water until the pH of the water phase is 6; and after separation, drying with anhydrous sodium sulfate, followed by additional drying in a vacuum at 40° C. to obtain the refined resin acids. The cyclohexylamine solution is prepared by dissolving cyclohexylamine in a quantity equal to the molar quantities of the resin acids contained in the pine oleoresin or rosin into 0.4 pbw of petroleum ether.

The pine oleoresin used as raw material in the present invention may be a form of pine oleoresin that contains pimaric type resin acids, such as *Pinus massoniana* pine oleoresin, *Pinus elliottii* pine oleoresin, *Pinus Caribaea* pine oleoresin, or *Pinus khasya* pine oleoresin, etc., wherein the pine oleoresin that is rich in pimaric type resin acids, such as *Pinus* elliottii pine oleoresin, is the best choice; the rosin used as raw material in the present invention may be rosin that contains pimaric type resin acids, such as *Pinus massoniana* rosin, *Pinus elliottii* rosin, *Pinus Caribaea* rosin, or *Pinus khasya* rosin, etc., wherein the rosin that is rich in pimaric type resin acids, such as *Pinus elliottii* rosin, is the best choice; the rosin may be gum rosin, tall oil rosin, or wood rosin; and the resin acids used as raw material in the present invention are preferably refined resin acids obtained from pine oleoresin or rosin through pre-treatment including salinization, acidification, or recrystallization, etc.

The chemical structural formula of abietic acid type resin acids and the principle of maleation reaction are shown as follows:

magnetic field from the original random distribution state, wherein the orientation varies according to the frequency of the alternating electromagnetic field. In this process, molecules move and rub against each other to produce heat; at the same time, the polar molecules that have absorbed energy, transfer energy to other molecules when they collide with other molecules, causing increased medium temperature. Since the additional reaction duration using microwave assistance is relatively short and the transformation ratio of abietic acid type resin acids is as high as 97% or above, the content of abietic acid-type resin acids in the pimaric type resin acid product is very low. Therefore, the content and yield of the target products, which are pimaric type resin acids, are both

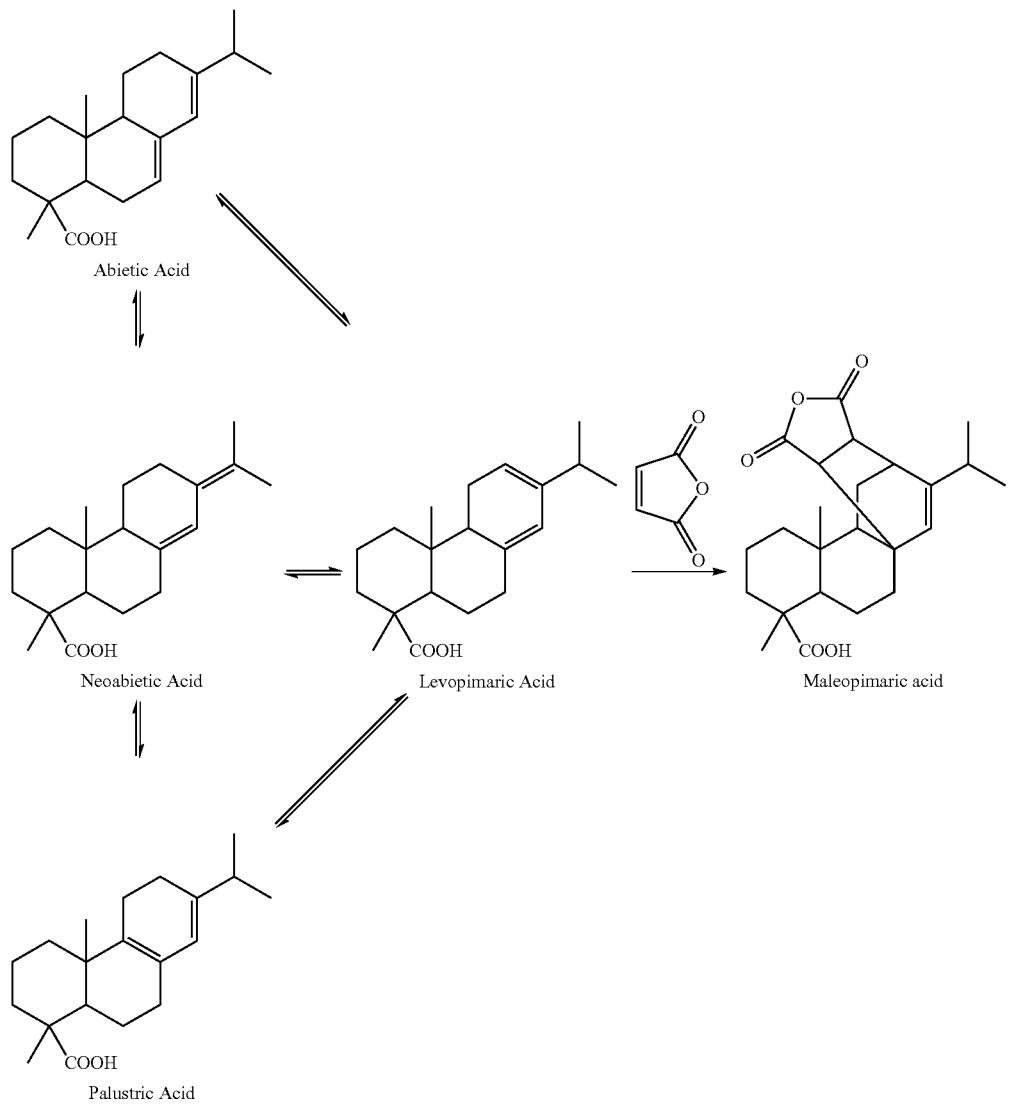

Beneficial Effects:

1. The present invention adopts microwave-assisted heating in maleation reaction, during which the abietic acid type resin acids in the raw material are transformed into maleopimaric acid. This transformation occurs because under the action of a high-frequency electromagnetic field, polar molecules tend to orient according to the polarity of the electroincreased, wherein, the content can be 93.5% or above, and the yield can be 64.4% or above.

2. The present invention uses $C_1$-$C_{10}$ lower fatty acid (e.g., glacial acetic acid) as the reaction medium, which absorbs microwave radiation nicely. This organic acid also has an acidic property having a catalytic effect to the maleation reaction, which therefore shortens the reaction time effectively, for example from original 4 hours or longer to 1 hour or shorter; facilitates the transformation of abietic acid type resin acids into maleopimaric acid; and further increases the yield of the target products, which are pimaric type resin acids.

3. The present invention uses organic acid (e.g., glacial acetic acid) as the solvent for recrystallization, which facilitates most of the produced maleopimaric acid to be removed effectively. Thus, the adverse effect of a large quantity of maleopimaric acid entrained in the precipitation of the pH adjustment procedure is effectively reduced, and the quality of pimaric type resin acids can be greatly improved.

4. In the present invention, the crystallized product separated by recrystallization is maleopimaric acid, which can also be taken as a byproduct of the present invention. The content of the obtained maleopimaric acid is high, and has more active groups than resin acids. The maleopimaric acid has wide application prospects and high economic value in the market.

5. The solvent used in the technical method of the present invention has a low boiling point, therefore is easy to recover and reuse, and thus has less environmental pollution. This technical process has high operability and economic efficiency, as well as good industrial application prospects due to its variety of scale.

6. With the technical method provided in the present invention, by selecting appropriate pine oleoresin, rosin, or resin acids from different kinds of trees as the raw material, pimaric type resin acid products with different composition can be prepared to meet different demands.

BRIEF DESCRIPTION OF THE DRAWING

The drawing is a GC analytical spectrum of pimaric type resin acid product (treated with methyl ester), which is prepared from *Pinus massoniana* rosin.

The component peak numbers, corresponding GC retention times, and component names in the spectrum are: 1#, 41.38 min., pimaric methyl; 2#, 41.92 min., sandaracopimaric methyl; 3#, 43.30 min., isopimaric methyl; 4#, 44.80 min., dehydrogenated abietic methyl; and 5#, 46.54 min., abietic methyl.

DETAILED DESCRIPTION OF THE EMBODIMENTS

The present invention will be further described in as follows.

A method for preparing pimaric type resin acids from pine oleoresin or rosin, including gum rosin, tall oil rosin, wood rosin, preferably *Pinus elliottii* pine oleoresin, or *Pinus elliottii* pine rosin, wherein the pine oleoresin can be transformed into rosin by distilling off turpentine, and the pine oleoresin or rosin can be further pre-treated with salinization, acidification, or recrystallization to remove neutral substances to obtain purified and refined resin acids. Once the pine oleoresin, rosin, or refined resin acids are obtained, the method further comprises: dissolving the obtained in glacial acetic acid with a mass of 0.05-30 times the weight of the total resin acid of the pin oleoresin, rosin, or refined resin acids and maleic anhydride; adding maleic anhydride with a mass of 0.3-1.5 times the weight of the total resin acid of the pin oleoresin, rosin, or refined resin acids into the solution; assisting the maleation reaction with microwave heating; adding glacial acetic acid with a mass of 0.1-15 times the weight of the reaction product into the solution; cooling down, crystallizing, and filtering the precipitate, followed by washing the precipitate with glacial acetic acid having a mass of 0-10 times the weight of the precipitate to be washed. The method further comprises: combining the filtrate; removing the solvent by reduced pressure distillation; dissolving the obtained product in 10 wt %-40 wt % sodium hydroxide solution; diluting the solution with either distilled water or deionized water to a volume (in liters) of 10-500 times the raw material (pine oleoresin, rosin, or purified resin acids obtained from pine oleoresin through pre-treatment); slowly adding drops of hydrochloric acid while agitating until the pH is in the range of 6-14; filtering the large amount of produced precipitate; washing the precipitate with water; dissolving the precipitate in ether with a mass of 0.5-20 times the precipitate; once more washing the precipitate with water until the ether layer becomes neutral; drying the ether layer with a drying agent; distilling off ether at 1 atm; and then treating the residue by drying and recrystallizing in order to obtain pimaric type resin acids. The present invention will be further described in the following examples.

EXAMPLE 1

Preparation of Refined Resin Acids

Add 1 part by weight (pbw) of *Pinus elliottii* pine oleoresin into a three-neck flask with agitator and reflux condenser; add 2.5 pbw of petroleum ether with 60° C.-90° C. boiling range into the flask; agitate the solution at 40° C. until the *Pinus elliottii* pine oleoresin is dissolved completely; remove insoluble solid impurities by filtering before the solution cools down; remove water contained in the pine oleoresin from the filtrate with a separatory funnel; add the filtrate into a four-neck flask with agitator and reflux condenser; slowly add drops of cyclohexylamine solution while agitating to produce a large quantity of white precipitate of ammonium salt of resin acid, wherein the cyclohexylamine solution is prepared by dissolving cyclohexylamine, in a quantity equal to the molar quantities of the resin acids contained in the pine oleoresin, into 0.4 pbw of petroleum ether; agitate at 40° C. for 1 hour; cool down to room temperature; further cool down the solution in an ice water bath; perform vacuum filtration; wash the precipitate with 0.2 pbw of petroleum ether 3 times; dry the precipitate in a vacuum drying oven at 40° C.; grind the precipitate into powder; add the powder into a three-neck flask that contains 0.7 pbw of ether and is equipped with both a mechanical agitator and ball condenser; agitate to make the white powder suspend in ether; add drops of 2 mol/L hydrochloric acid solution into the flask at room temperature until the white powder disappears completely, and then agitate further for 30 minutes; transfer the mixture into a separatory funnel to remove the water layer; wash with distilled water repeatedly until the pH of the water phase is 6; remove the water layer and dry the mixture with anhydrous sodium sulfate; distil at 1 atm to remove most of the ether in the organic phase; transfer the concentrated solution into a watch glass; and dry in a vacuum at 40° C. to obtain refined resin acids. Once the refined resin acids are obtained, take samples for use in performing both a GC analysis and a GC-MS analysis.

The samples for GC and GC-MS analysis are pre-treated with methyl ester as follows: dissolve the sample in methanol solution; add phenolphthalein as an indicator; and add 6 wt % methanol solution of tetramethyl ammonium hydroxide in drops until the sample turns to a pink color and the pink color doesn't fade within 30 seconds.

The condition for GC and GC-MS analysis is as follows: a two-stage program is employed for heating-up; in the first stage, the initial temperature is 150° C., the heating-up rate is 5° C./min, the final temperature is 220° C., and the holding time is 0 minutes; in the second stage, the heating-up rate is 1° C./min, the final temperature is 270° C., and the holding time is 15 minutes. The temperature in the vaporizing chamber and the temperature of detector are both 260° C., the split ratio is 64:1, the sample size is 0.8 µL, the relevant components of pimaric type resin acids are determined by the GC-MS analysis, and the mass fraction of pimaric type resin acids is measured with the GC normalized method. The result of analysis indicates that the total mass fraction of pimaric type resin acids in the *Pinus elliottii* pine resin acids is 19.10 wt %.

EXAMPLE 2

Preparation of Refined Resin Acids

The *Pinus elliottii* pine oleoresin used in example 1 is replaced with *Pinus massoniana* pine oleoresin, while the rest of the operations are the same as those in example 1. The result of the analysis indicates that the total mass fraction of pimaric type resin acids in the *Pinus massoniana* pine resin acids is 7.76 wt %.

EXAMPLE 3

Add 20.1 g of refined resin acids, prepared according to example 1, into a special microwave reaction bulb; add 8.1 g of maleic anhydride and 8.2 g of glacial acetic acid; agitate until the added substances are dissolved completely; arrange the microwave reaction bulb containing the material in a microwave reactor with a reflux condenser; adjust the microwave power to 120 W; after reacting for 28 minutes, take out the reaction bulb from the microwave reactor; add 47.2 g of glacial acetic acid into the reaction bulb; cool down the solution and let it crystallize; filter the solution; wash the precipitate with 5 g of glacial acetic acid; combine the filtrate; distil the solvent at reduced pressure, and then dissolve it in 28 wt % of sodium hydroxide solution; add water to dilute the solution to 1000 mL; slowly add drops of hydrochloric acid while agitating until the pH reaches 7.5; filter the precipitate and wash it with water; add 17 g of ether to dissolve the precipitate; wash with water until the pH of the ether layer reaches 8; dry the ether layer with anhydrous sodium sulfate; distil off ether at 1 atm; and vacuum dry to obtain 3.3 g of pimaric type resin acids. Of the mass fraction of the pimaric type resin acids in the raw material of refined resin acids, the yield of the pimaric type resin acids is 63.70% of the theoretical yield. The result of GC analysis indicates the mass fraction of pimaric type resin acids in the obtained pimaric type resin acid product is 75.7%.

EXAMPLE 4

Add 20.0 g of refined resin acids, prepared according to example 1, into a special microwave reaction bulb; add 8.0 g of maleic anhydride and 8.0 g of glacial acetic acid; agitate until the added substances are dissolved completely; arrange the microwave reaction bulb containing the material in a microwave reactor with a reflux condenser; adjust the microwave power to 120 W; after reacting for 25 minutes, take out the reaction bulb from the microwave reactor; add 10.0 g of glacial acetic acid into the reaction bulb; cool down the solution and let it crystallize; filter the solution; wash the precipitate with 6.0 g of glacial acetic acid; combine the filtrate; distil the solvent at reduced pressure, and then dissolve it in 20 wt % of sodium hydroxide solution; add water to dilute the solution to 1000 mL; slowly add drops of hydrochloric acid while agitating until the pH reaches 8.5; filter the precipitate and wash it with water; add 15.0 g of ether to dissolve the precipitate; wash with water until the ether layer becomes neutral (pH=7); dry the ether layer with anhydrous magnesium sulfate; distil off ether at 1 atm; and vacuum dry to obtain 2.8 g of pimaric type resin acid product. The yield of pimaric type resin acids is 61.8% of the theoretical yield. The result of GC analysis indicates the mass fraction of pimaric type resin acids is 84.30%.

EXAMPLE 5

Add 50.0 g of refined resin acids, prepared according to example 2, into a special microwave reaction bulb; add 20.0 g of maleic anhydride and 20.0 g of glacial acetic acid; agitate until the added substances are dissolved completely; arrange the microwave reaction bulb containing the material in a microwave reactor with a reflux condenser; adjust the microwave power to 120 W; after reacting for 30 minutes, take out the reaction bulb from the microwave reactor; add 20.0 g of glacial acetic acid into the reaction bulb; cool down the solution and let it crystallize; filter the solution; wash the precipitate with 10.0 g of glacial acetic acid; combine the filtrate; distil the solvent at reduced pressure, and then dissolve in 35 wt % of sodium hydroxide solution; add water to dilute the solution to 1000 mL; slowly add drops of hydrochloric acid while agitating until the pH reaches 9; filter the precipitate and wash it with water; add 20.0 g of ether to dissolve the precipitate; wash with water until the ether layer becomes neutral (pH=7); dry the ether layer with anhydrous sodium sulfate; distil off ether at 1 atm; and vacuum dry to obtain 2.5 g of pimaric type resin acid product. The yield of the pimaric type resin acids is 64.4% of the theoretical yield. The result of GC analysis (shown in the drawing) indicates the mass fraction of pimaric type resin acids is 93.56%.

EXAMPLE 6

Add 20.1 g of *Pinus elliottii* rosin into a special microwave reaction bulb; add 7.8 g of maleic anhydride and 8.2 g of glacial acetic acid; agitate until the added substances are dissolved completely; arrange the microwave reaction bulb containing the material in a microwave reactor with a reflux condenser; adjust the microwave power to 120 W; after reacting for 30 minutes, take out the reaction bulb from the microwave reactor; add 20.0 g of glacial acetic acid into the reaction bulb; cool down the solution and let it crystallize; filter the solution; wash the precipitate with 5.0 g of glacial acetic acid; combine the filtrate; distil the solvent at reduced pressure; wash the filtrate with 80% ethanol 2 times; filter the products; dry the filter residue in a vacuum and then dissolve it in 28 wt % of sodium hydroxide solution; add water to dilute the solution to 1000 mL; slowly add drops of hydrochloric acid while agitating until the pH reaches 8.2; filter the large amount of precipitate and wash it with water; add 17.0 g of ether to dissolve the precipitate; wash with water until the ether layer becomes neutral (pH=7); dry the ether layer with anhydrous sodium sulfate; distil off ether at 1 atm; and vacuum dry to obtain 1.8 g of pimaric type resin acid product. The yield of the pimaric type resin acids is 44.2% of the theoretical yield. The result of GC analysis indicates the mass fraction of pimaric type resin acids is 78.5%.

EXAMPLE 7

Add 1 pbw of *Pinus Caribaea* pine rosin into a three-neck flask with an agitator and reflux condenser; add 2.5 pbw of petroleum ether with 60° C.-90° C. boiling range into the flask; agitate the solution at 40° C. until the *Pinus Caribaea* pine oleoresin is dissolved completely; remove insoluble solid impurities from the rosin by filtering before the solution cools down; remove water contained in the rosin from the filtrate with a separatory funnel; add the filtrate into a four-neck flask with agitator and reflux condenser; slowly add drops of cyclohexylamine solution while agitating to produce a large quantity of white precipitate of ammonium salt of resin acid, wherein the cyclohexylamine solution is prepared by dissolving cyclohexylamine in a quantity equal to the molar quantities of resin acids contained in the rosin into 0.4 pbw of petroleum ether, agitate for 1 hour at 40° C.; cool down to room temperature; further cool down the solution in an ice water bath; perform vacuum filtration; wash the precipitate with 0.2 pbw of petroleum ether 3 times; dry the precipitate in a vacuum drying oven at 40° C.; grind the precipitate into powder; add the powder into a three-neck flask containing 0.7 pbw of ether and is equipped with a mechanical agitator and ball condenser; agitate to make the white powder suspend in ether; add drops of 2 mol/L hydrochloric acid solution into the flask at room temperature until the white powder disappears completely; agitate further for 30 minutes; transfer the mixture into a separatory funnel to remove the water layer; wash with distilled water repeatedly until the pH of the water phase reaches 6; remove the water layer and dry the mixture with anhydrous sodium sulfate; distil at 1 atm to remove most of the ether in the organic phase; transfer the concentrated solution into a watch glass; and dry in a vacuum at 40° C. to obtain the refined resin acids.

EXAMPLE 8

Add 20.0 g of refined resin acids into a special microwave reaction bulb; add 8.0 g of maleic anhydride and 8.0 g of butyric acid; agitate until the added substances are dissolved completely; arrange the microwave reaction bulb containing the material in a microwave reactor with a reflux condenser; adjust the microwave power to 120 W; after reacting for 25 minutes, take out the reaction bulb from the microwave reactor; add 10.0 g of butyric acid into the reaction bulb; cool down the solution and let it crystallize; filter the solution; wash the precipitate with 6.0 g of butyric acid; combine the filtrate; distil the solvent at reduced pressure, and then dissolve in 2 wt % of sodium hydroxide solution; add water to dilute the solution to 1000 mL; slowly add drops of 20 wt % of sulfuric acid while agitating until the pH reaches 8.5; filter and wash the precipitate with water; add 15.0 g of ether to dissolve the precipitate; wash with water until the ether layer becomes neutral (pH=7); dry the ether layer with anhydrous magnesium sulfate; distil off ether at 1 atm; and vacuum dry to obtain pimaric type resin acid product.

EXAMPLE 9

Add 1 pbw of *Pinus khasya* pine oleoresin into a three-neck flask with an agitator and reflux condenser; add 2.5 pbw of petroleum ether with 60° C.-90° C. boiling range into the flask; agitate the solution at 40° C. until the *Pinus khasya* pine oleoresin is dissolved completely; remove insoluble solid impurities from the pine oleoresin by filtering before the solution cools down; remove water contained in pine oleoresin from the filtrate with a separatory funnel; add the filtrate into a four-neck flask with an agitator and reflux condenser; slowly add drops of cyclohexylamine solution while agitating to produce a large quantity of white precipitate of ammonium salt of resin acid, wherein, the cyclohexylamine solution is prepared by dissolving cyclohexylamine in a quantity equal to the molar quantities of resin acids contained in the pine oleoresin into 0.4 pbw of petroleum ether; agitate for 1 hour at 40° C.; cool down to room temperature; further cool down the solution in an ice water bath; perform vacuum filtration; wash the precipitate with 0.2 pbw of petroleum ether 3 times; dry the precipitate in a vacuum drying oven at 40° C.; grind the precipitate into powder; add the powder into a three-neck flask that contains 0.7 pbw of ether and is equipped with a mechanical agitator and ball condenser; agitate to make the white powder suspend in ether; add drops of 2 mol/L hydrochloric acid solution into the flask at room temperature until the white powder disappears completely, further agitate for 30 minutes; transfer the mixture into a separatory funnel to remove the water layer; wash with distilled water repeatedly until the pH of the water phase reaches 6; remove the water layer and dry the mixture with anhydrous sodium sulfate; distil at 1 atm to remove most of ether in the organic phase; transfer the concentrated solution into a watch glass; and dry in a vacuum at 40° C. to obtain refined resin acids.

EXAMPLE 10

Add 20.0 g of refined resin acids into a special microwave reaction bulb; add 8.0 g of maleic anhydride and 8.0 g of propionic acid; agitate until the added substances are dissolved completely; arrange the microwave reaction bulb containing the material in a microwave reactor with a reflux condenser; adjust the microwave power to 120 W; after reacting for 25 minutes, take out the reaction bulb from the microwave reactor; add 10.0 g of propionic acid into the reaction bulb; cool down the solution and let it crystallize; filter and wash the precipitate with 6.0 g of propionic acid; combine the filtrate; distil the solvent at reduced pressure and then dissolve in 40 wt % of sodium hydroxide solution; add water to dilute the solution to 1000 mL; slowly add drops of 1 wt % hydrochloric acid while agitating until the pH reaches 8.5; filter the precipitate and wash it with water; add 15.0 g of ether to dissolve the precipitate; wash with water until the ether layer becomes neutral (pH=7); dry the ether layer with anhydrous magnesium sulfate; distil off ether at 1 atm; and vacuum dry to obtain pimaric type resin acid product.

The invention claimed is:
1. A method for preparing pimaric type resin acids, the method comprising:
adding refined resin acids, pine oleoresin, or rosin, along with maleic anhydride at a mass ratio of 1:0.3-1.5 into a reaction bulb, dissolving them into a $C_1$-$C_{10}$ lower fatty acid solvent, the mass ratio between the $C_1$-$C_{10}$ lower fatty acid solvent and refined resin acids, pine oleoresin, or rosin is 0.05-30:1, and then performing an additive reaction under either microwave-assisted heating or direct heating, after the reaction, allowing the solution to cool down and form crystallized material, then filtering and washing the crystallized material; and
combining the filtrate collected from filtering and washing, performing a reduced pressure distillation using the filtrate collected to remove the solvent and obtaining a crude product of pimaric type resin acids, dissolving the crude product of pimaric type resin acids in sodium hydroxide solution to produce a solution of pimaric type resin acids, adjusting the pH of the solution of pimaric type resin acids to around 6-14 using mineral acid or organic acid during agitation to produce precipitates, and purifying the obtained precipitates to obtain a final product of pimaric type resin acids, wherein the final product of pimaric type resin acids comprises a mixture of pimaric type resin acids.

2. The method according to claim 1, wherein the additive reaction is performed under microwave-assisted heating and the condition of microwave-assisted heating is as follows: the microwave power is 100W-50 kW, and the reaction time under microwave-assisted heating is from 5 minutes to 300 minutes.

3. The method according to claim 1, wherein refined resin acids are used and the refined resin acids are products obtained by removing neutrals from the pine oleoresin or the rosin by recrystallization in organic solvent, and treating the neutrals with sodium salt and/or ammonium salt, and/or washing the neutrals with organic solvent.

4. The method according to claim 3, wherein the pine oleoresin is any one of *Pinus massoniana* pine oleoresin, *Pinus elliottii* pine oleoresin, *Pinus Caribaea* pine oleoresin, or *Pinus khasya* pine oleoresin; and the rosin is any one of gum rosin, tall oil rosin, or wood rosin which are produced from *Pinus massoniana* pine, *Pinus Caribaea* pine, *Pinus khasya* pine, or *Pinus elliottii* pine.

5. The method according to claim 1, wherein the $C_1$-$C_{10}$ lower fatty acid solvent is any one of glacial acetic acid, propionic acid, or butyric acid.

6. The method according to claim 1, wherein the concentration of the sodium hydroxide solution is 0.5%-40%.

7. The method according to claim 1, wherein the mineral acid is hydrochloric acid or sulfuric acid, the organic acid is formic acid or acetic acid, and the concentration of the acid is 0.5%-100%.

8. The method according to claim 1, wherein the purifying of the obtained precipitate to obtain the final product of pimaric type resin acids includes dissolving the precipitate in ether with a mass of 0.5-20 times the mass of the precipitate; washing with water until the ether layer becomes neutral; drying with anhydrous magnesium sulfate;
distilling off ether at 1 atm; and then drying in a vacuum to obtain the final product of pimaric type resin acids.

9. The method of claim 1, wherein the final produce of pimaric type resin acids contains at least 93.5% pimaric type resin acids, and a yield of at least 64.4%.

* * * * *